United States Patent [19]

Hayes

[11] Patent Number: 5,279,819
[45] Date of Patent: Jan. 18, 1994

[54] SHAVING COMPOSITIONS

[75] Inventor: Marilyn J. Hayes, Melrose, Mass.

[73] Assignee: The Gillette Company, Boston, Mass.

[21] Appl. No.: 947,966

[22] Filed: Sep. 21, 1992

Related U.S. Application Data

[63] Continuation of Ser. No. 847,390, Mar. 6, 1992, abandoned, which is a continuation-in-part of Ser. No. 670,848, Mar. 18, 1991, abandoned.

[51] Int. Cl.$^5$ ................................................ A61K 7/15
[52] U.S. Cl. ..................................... 424/73; 424/45; 424/47; 514/938; 514/939; 514/945
[58] Field of Search ................. 424/73, 47; 514/938, 514/939, 940, 945; 252/309, 310, 312

[56] References Cited

U.S. PATENT DOCUMENTS

| | | | |
|---|---|---|---|
| 3,923,970 | 12/1975 | Breuer | 424/47 |
| 3,959,160 | 5/1976 | Horsler et al. | 252/90 |
| 4,145,411 | 3/1979 | Mende | 424/73 |
| 4,423,041 | 12/1983 | Clum et al. | 252/312 |
| 4,686,099 | 8/1987 | Palinczar | 424/59 |
| 4,720,353 | 1/1988 | Bell | 514/887 |
| 4,957,732 | 9/1990 | Grollier et al. | 424/73 |

*Primary Examiner*—Thurman K. Page
*Assistant Examiner*—James M. Spear
*Attorney, Agent, or Firm*—Stephan P. Williams; Mandel Slater

[57] ABSTRACT

An improved instant foaming aerosol shave cream is provided which includes, in percent by weight of the entire composition, (a) about 70–90% water, (b) about 10–20% of a soap component comprising about 8–12% of an alkanolamine $C_{14}$-$C_{18}$ fatty acid soap and about 2–4% of a nonionic surfactant having an HLB of at least about 15, (c) about 1–5% of a propellant having a vapor pressure of about 30–60 Psig at 70° F., (d) about 0.1–5% of one or more emollients, and (e) about 0.3–4% of a foam stabilizer component comprising about 0.1–3% of a fatty alcohol, about 0.1–3% of a fatty alkanolamide, and about 0.01–0.6% of a fatty acid diester of polyethylene glycol having a molecular weight of at least about 1000. The compositions are oil-in-water emulsions and exhibit advantages associated with delayed-foaming shaving gels but with the convenience of instant foams.

10 Claims, No Drawings

SHAVING COMPOSITIONS

This application is a continuation of Ser. No. 07/847,390 filed Mar. 6, 1992, now abandoned, which is a continuation-in-part of Ser. No. 07/670,848 filed Mar. 18, 1991, now abandoned.

FIELD OF THE INVENTION

This invention relates to improved compositions for wet shaving, i.e., shaving with a razor blade, the compositions being adapted for packaging in a pressurized aerosol container and dispensing as a shave cream of the instant foaming type.

BACKGROUND OF THE INVENTION

The main requirements of a wet shaving preparation are to maintain the beard in softened condition, to lubricate the passage of the razor over the face, and, it has been suggested, to support the beard hair for cutting. In addition, the preparation should not irritate the skin, should be easily rinsed from the razor and the face, should be stable over a range of temperatures, non-corrosive to the razor blade, and resistant to premature drying out and collapse.

Currently the most widely used form of shaving preparation is the type referred to herein as an instant foam, which is dispensed from a pressurized aerosol container in the form of a rich lather for spreading on the area to be shaved, which preferably has been washed and left wet to further help soften and prepare the beard. The essential ingredients of such a composition are water, a soap component, which may comprise anionic, cationic, amphoteric, or nonionic surfactants and permitted combinations thereof, and a propellant. The constituents of the soap component, as well as the other ingredients of the composition, are so selected, as is now well known in the art, such that an instant foam shave preparation having excellent performance attributes may readily be formulated. The same essential ingredients, appropriately selected and in appropriate concentrations, with or without the addition of a water-soluble polymer as a gelling agent, can be formulated to make a composition for a self-foaming gel (often called a "post-foaming gel" and the propellant referred to in this context as the "post-foaming agent"), a shave preparation product form that has achieved For an extensive discussion of the formulation of shaving Preparations, including instant foams and self-foaming gels, reference may be made to *Harry's Cosmeticology*, J. B. Wilkinson and R. J. Moore, eds., 7th edition, Chemical Publishing Co., N.Y., 1982, pp. 156–175, which is herein fully incorporated by reference.

The two above-mentioned product forms, often referred to simply as foams and gels, together dominate the marketplace for wet shave preparations, the combined lather and brushless creams, soap sticks, and other product forms now accounting for only a fairly small share of market. It has been suggested among those preferring gels that this product form provides a smoother, closer, more comfortable shave, with fewer nicks and cuts. Devotees of foams tend to like having the product already foamed as it comes out of the can so that it doesn't have to be worked into a lather by spreading, plus easy spread and rinsing qualities, and the absence of the cold feel of a gel. Consequently there is a continuing effort to develop improved shaving preparations that would combine, in one product, the advantages associated with both the best foams and gels.

SUMMARY OF THE INVENTION

It has been found that the relative advantages of foams and gels can be obtained in an aerosol shave cream composition of the instant foaming type which is an oil-in-water emulsion and includes, in percent by weight of the entire composition, (a) about 70–90% water, (b) about 10–20% of a soap component comprising about 8–12% of an alkanolamine $C_{14}$–$C_{18}$ fatty acid soap and about 2–4% of a nonionic surfactant having an HLB of at least about 15, (c) about 1–5% of a propellant having a vapor pressure of about 30–60 Psig at 70° F., (d) about 0.1–5% of one or more emollients, and (e) about 0.3–4% of a foam stabilizer component comprising about 0.1–3% of a fatty alcohol, about 0.1–3% of a fatty alkanolamide, and about 0.01–0.6% of a fatty acid diester of polyethylene glycol having a molecular weight of at least about 1000. As noted, the compositions exhibit advantages associated with delayed foaming shaving gels but with the convenience of instant foams.

It is not inappropriate to refer to a composition according to the present invention as an "instant foaming gel" due to certain similarities with the delayed foaming shave gels. One such area of similarity is the composition of the inventive formulations, which will be recognized by those skilled in the art as similar in certain respects to typical formulations for shaving gels, the main differences being in adjusting the soap component or surfactant blend somewhat with respect to selection and reduced concentration to avoid gellation, as well as selecting a more volatile propellant (self-foaming agent) to insure instant rather than delayed conversion to a foam on expulsion from the aerosol container. Another similarity is the close correlation in the manufacturing process between gels and compositions of the present invention. Yet another similarity that will also be appreciated by those skilled in the art relates to mineral oil, which is known to adversely affect the foam properties of instant foams (tends to cause billowing and soft body), but is commonly used in gels. However, mineral oil is a preferred emollient in compositions according to the present invention; it does not adversely affect foam quality and enhances shave performance.

Foam stiffness, which is a measure of the force required to push a plunger through a material under test, is another area of anomalous behavior for the shave foams of the present invention. In order to understand the numerical stiffness values obtained, the foam stiffness measurement will now be described. The measurement uses a Model LFRA Texture Analyzer (Texture Technologies Corp., Scarsdale, N.Y.) fitted with a $1\frac{1}{2}''$ diameter cylindrical plunger. The test sample is a fresh shot of shaving foam dispensed into and completely filling an open cup about $2\frac{1}{4}''$ in diameter, about $1\frac{3}{4}''$ height, and having a volume of about 140 ml. The foam in the cup is leveled by passing a straight edge across the top, and the cup is immediately placed on the anvil of the texture analyzer centered under the plunger. The plunger is then promptly actuated to travel vertically downward through the shave foam for a total distance of 19 mm at a rate of 2 mm/sec, and the peak force required to move the plunger through the foam is recorded (grams).

Conventional aerosol instant foam shave creams exhibit foam stiffness of about 60–90 grams, dropping gradually over can life from a point near the upper end of this range and then more precipitously near the end of can life to a point near the lower end of this range. In contrast the inventive shave foams exhibit stiffness values in the range of about 110-200 grams and remain substantially more uniform over the life of the can, a beginning-to-end uniformity more characteristic of the self-foaming shave gels as a class. Moreover, these high stiffness values in an instant foam suggest an overly stiff foam that even looks that way to the eye and appears as though a dollop would fall from the hand, yet it spreads well and feels nice on the skin.

The major essential component of the inventive instant foaming aerosol shave cream is about 70-90%, preferably about 75-85% by weight of water, which is preferably deionized or distilled water free of dissolved electrolytes such as salts and acids. The water component is essential to provide adequate solubility for the soap component and compatibility with the other essential ingredients and to provide a stable shaving composition having the desired foaming properties and capable of being readily rinsed from the skin.

The soap component of the composition, for the purposes hereof, includes in combination both a water-soluble alkanolamine salt of a $C_{14}$-$C_{18}$ fatty acid and any of certain, usually synthetic, nonionic wetting agents or surfactants; the combination is designated the soap component or, simply, the soap. All of these materials are well known in the art. The soap comprises about 10-20%, preferably about 11-15% by weight of the total composition. The water-soluble alkanolamine fatty acid salts should comprise about 8-12% by weight of the total composition. They may be preformed or formed in situ by reacting a basic material such as triethanolamine, monoethanolamine, or other alkanolamine or combination selected from the group of alkanolamines identified at pp. 3-4 of the *CTFA Cosmetic Ingredient Handbook* (1st ed., 1988, published by The Cosmetic, Toiletry and Fragrance Association, Inc., Washington, D.C.) with a higher fatty acid such as stearic, palmitic, myristic, oleic, coconut oil fatty acids, and mixtures thereof. Triethanolamine soaps of stearic, palmitic, and myristic acids are preferred, with triethanolamine palmitate particularly preferred. The nonionic surfactants that are useful as a portion of the soap component should comprise about 2-4% by weight of the total composition, should have a fairly high HLB, at least about 15, and should be appreciably soluble in the aqueous components of the composition. Many such materials are available in the art and include nonionic surfactants from such classes as water-soluble polyoxyethylene ethers of alkyl-substituted phenols and water-soluble polyethoxylated fatty alcohols and polyols. Laureth-23 (HLB 16.9) and Polysorbate 80 (HLB 15.0) are particularly preferred, although substitutions and combinations from the specified classes may be made in particular compositions. (Chemical names as used herein follow the system of nomenclature adopted by the Cosmetic, Toiletry and Fragrance Association, Inc. ("CFTA").)

Another essential component of the aerosol shave cream compositions of the present invention is about 1-5%, preferably about 2-4% by weight, of a volatile propellant which preferably is a hydrocarbon or hydrocarbon blend selected from the group consisting of n-butane, isobutane, propane, and mixtures thereof and having a vapor pressure of about 30-60 Psig at 70° F. As is well known in the art, the propellant serves both to expel the product concentrate from the can and instantly convert it to a rich foam or lather for shaving. A preferred propellant identified by the industry designation A-46 is a mixture of n-butane, isobutane, and propane in proportions chosen such that the blend has a vapor pressure of 46 Psig at 70° F.

The emollient component of the composition serves to smooth and protect the skin and make it feel soft and supple. It should comprise about 0.1-5%, preferably about 1-2.5% by weight of the composition and include one or more of such materials as mineral oil, dimethicone copolyols, fatty acid esters, lanolin, branched-chain hydrocarbons, and the like. An emollient blend of about 0.06-3.5%, preferably about 0.75-1.5% of a mineral oil and about 0.04-2% preferable 0.3-1%, of a cetyl dimethicone copolyol (available as Abil EM-90 from Goldschmidt Chemical Corp., Hopewell, Va.) as the major emollient gives particularly good results. As particularly useful emollients mention may also be made of propylene glycol isostearate and hydrogenated polyisobutene (Panalane L-14E, Amoco Chemical Company, Chicago, Ill.). It should be noted, as will be appreciated by those skilled in the art, that the classification of ingredients in complex compositions of the type herein described is necessarily somewhat arbitrary. For example, cetyl dimethicone copolyol is also properly characterized as a surfactant. Consequently, for the purposes hereof, the components of the inventive compositions are characterized according to what is believed to be their principal roles in providing the desired characteristics of such compositions.

The foam stabilizer (or foam modifier) component comprises about 0.3-4%, preferably about 1-2.5% by weight, of the composition and is a blend including about 0.1-3% preferable 0.2-2% of a fatty alcohol, about 0.1-3%, preferably about 0.25-1% of a fatty alkanolamide, and about 0.01-0.6%, preferably about 0.1-0.3% by weight of a fatty acid diester of polyethylene glycol having a molecular weight of at least about 1000, preferably at least about 6000. In preferred embodiments of the invention the fatty alcohol should have 12-18 carbon atoms, with stearyl alcohol particularly preferred; the alcohol adds whiteness, foam body, and imparts lubricity to the formulation. The fatty alkanolamide contributes to the thickness and creaminess of the foam and to a lesser extent is thought to provide some skin conditioning benefits in addition to the emollients; suitable alkanolamides are usually chosen from the group of these materials listed on page 3 of the above-referenced *CTFA Cosmetic Ingredient Handbook*, while preferred members of the class include stearmide DEA and MEA and lauramide DEA and MEA, with lauramide DEA particularly preferred. The fatty acid diester of polyethylene glycol should have a molecular weight of at least about 1000, preferably at least about 6000, with PEG-150 distearate particularly preferred.

Other compatible additives as are well known in the art for use in shaving preparations may also be included in minor proportions so long as they do not adversely affect the properties of the composition. As examples of such additives, mention may be made of humectants, such as glycerin and sorbitol; skin freshening and skin soothing ingredients, such as menthol, aloe, and lanoline; preservatives, such as BHA and BHT; perfume, colorants, opacifiers, and clarifying agents as desired; and antiseptic agents.

The following Examples illustrate representative shave cream compositions according to the invention and are given by way of illustration only and are not to be considered as being limiting. The amounts in the Examples and the claims are in weight percent.

EXAMPLE I

| (Instant foaming aerosol shave foam) | |
|---|---|
| CTFA Name | Percent Active |
| Water | 80.24 |
| Palmitic Acid | 6.58 |
| Triethanolamine (99%) | 3.39 |
| Laureth-23 | 2.90 |
| Propellant A-46 | 3.24 |
| Cetyl Dimethicone Copolyol (Abil EM-90) | 0.58 |
| Mineral Oil | 0.97 |
| Stearyl Alcohol | 0.97 |
| Lauramide DEA | 0.48 |
| PEG-150 Distearate | 0.15 |
| Fragrance | 0.48 |
| BHT | 0.02 |
| | 100.00% |

Procedure: (1) Aqueous phase: Heat the water to 80°-85° C., and add palmitic acid. Melt. Add laureth-23, melt, and mix well. Add triethanolamine and mix well (about 15 min.) to form the soap. (2) Oil phase: Mix, heat, and blend at about 55° C. the stearyl alcohol, mineral oil, lauramide DEA, cetyl dimethicone copolyol, PEG-150 distearate, and BHT. (3) Add oil phase to aqueous phase maintained at 80° C. and mix well (about 15 min.). (4) Cool to room temperature and add fragrance. (5) Package with the propellant in aerosol cans, with 5-minute mechanical shake.

The product of the Example dispensed as a thick, rich, creamy foam with a substantially constant stiffness of 110-150 grams throughout can life. The foam spread and rinsed well, felt good on the face, and gave a smooth, close shave with better skin protection than conventional aerosol foams.

The following additional compositions according to the invention were also prepared. The procedure was similar to that given for Example I:

| | Percent Active | |
|---|---|---|
| Ingredient | Example II | Example III |
| Water | 79.61 | 80.24 |
| Palmitic Acid | 6.58 | 6.58 |
| Triethanolamine (99%) | 3.39 | 3.39 |
| Laureth-23 | 2.90 | — |
| Polysorbate 80 | — | 2.90 |
| Propellant A-46 | 3.24 | 3.24 |
| Stearyl Alcohol | 0.97 | 0.97 |
| Cetyl Dimethicone Copolyol | — | 0.58 |
| Mineral Oil | 0.97 | — |
| Propylene Glycol Isostearate | 0.58 | — |
| Hydrogenated Polyisobutene | — | 0.97 |
| Lauramide DEA | 0.97 | 0.48 |
| PEG-150 Distearate | 0.29 | 0.15 |
| Fragrance | 0.48 | 0.48 |
| BHT | 0.02 | 0.02 |
| | 100% | 100% |

While particular embodiments of the invention have been shown and described, various modifications will be apparent to those skilled in the art, and therefore it is not intended that the invention be limited to the disclosed embodiments or to details thereof, and departures may be made therefrom within the spirit and scope of the invention.

What is claimed is:

1. A composition in the form of an oil-in-water emulsion and suitable for packaging in a pressurized aerosol container and dispensing as an instant-foaming shave cream which comprises, in percent by weight of the entire composition,
    (a) about 70-90% water,
    (b) about 10-12% of a soap component which includes about 8-12% of an alkanolamine soap of a $C_{14}$-$C_{18}$ fatty acid and about 2-4% of a nonionic surfactant having an HLB of at least about 15,
    (c) about 1-5% of a propellant having a vapor pressure of about 30-60 Psig at 70° F.,
    (d) about 0.1-5% of one or more emollients, and
    (e) about 0.3-4% of a foam stabilizer component consisting essentially of about 0.1-3% of a fatty alcohol, about 0.1-3% of a fatty alkanolamide, and about 0.01-0.6% of a fatty acid diester of polyethylene glycol having a molecular weight of at least about 1000.
2. The composition of claim 1 having a foam stiffness in the range of about 110-200 grams.
3. The composition of claim 2 in which said nonionic surfactant comprises a polyethoxylated fatty alcohol.
4. The composition of claim 2 in which said emollients comprise about 0.04-2% of a cetyl dimethicone copolyol and about 0.06-3.5% of a mineral oil.
5. The composition of claim 2, in which said fatty alcohol comprises stearyl alcohol, said fatty alkanolamide comprises lauramide DEA and said fatty acid diester comprises a stearic acid diester with a molecular weight of at least about 6000.
6. A composition in the form of an oil-in-water emulsion and suitable for packaging in a pressurized aerosol container and dispensing as an instant-foaming shave cream, said composition having a foam stiffness in the range of 110-200 grams and comprising, in percent by weight of the entire composition,
    (a) about 75-85% water,
    (b) about 11-15% of a soap component which includes about 8-12% of a triethanolamine soap of a $C_{14}$-$C_{18}$ fatty acid and about 2-4% of a polyethoxylated fatty alcohol having an HLB of at least about 15,
    (c) about 2-4% of a propellant having a vapor pressure of about 30-60 Psig at 70° F.,
    (d) about 1-2.5% of an emollient component, and
    (e) about 1-2.5% of a foam stabilizer component consisting essentially of about 0.2-2% of a fatty alcohol, about 0.25-1% of a fatty alkanolamide, and about 0.1-0.3% of a fatty acid diester of polyethylene glycol having a molecular weight of at least about 6000.
7. The composition of claim 6 wherein said emollient component includes about 0.75-1.5% of a mineral oil and about 0.3-1% of a cetyl dimethicone copolyol.
8. The composition of claim 6 wherein said fatty alcohol comprises stearyl alcohol, said fatty alkanolamide comprises lauramide DEA and said fatty acid diester comprises a stearic acid diester with a molecular weight of at least about 6000.
9. The composition of claim 7 wherein said fatty alcohol comprises stearyl alcohol, said fatty alkanolamide comprises lauramide DEA and said fatty acid diester comprises a stearic acid diester with a molecular weight of at least about 6000.
10. The composition of claim 9 wherein said alkanolamine soap is triethanolamine palmitate and said nonionic surfactant is Laureth-23.

* * * * *

UNITED STATES PATENT AND TRADEMARK OFFICE
CERTIFICATE OF CORRECTION

PATENT NO. : 5,279,819

DATED : January 18, 1994

INVENTOR(S) : Marilyn J. Hayes

It is certified that error appears in the above-identified patent and that said Letters Patent is hereby corrected as shown below:

Col. 6, line 7, change "10-12%" to read -- 10-20% --.

Signed and Sealed this

Thirteenth Day of September, 1994

Attest:

BRUCE LEHMAN

Attesting Officer

Commissioner of Patents and Trademarks